United States Patent

Nordell, II et al.

[11] Patent Number: 5,816,095
[45] Date of Patent: Oct. 6, 1998

[54] BENDING TOOL

[75] Inventors: Benjamin T. Nordell, II, Menlo Park; Rick T. Smethers, Fremont, both of Calif.

[73] Assignee: Somnus Medical Technologies, Inc., Sunnyvale, Calif.

[21] Appl. No.: 941,403

[22] Filed: Sep. 30, 1997

[51] Int. Cl.⁶ .................................................. B21D 7/022
[52] U.S. Cl. ............................ 72/458; 72/479; 140/123
[58] Field of Search ........................... 72/457, 458, 459, 72/479; 140/123

[56] References Cited

U.S. PATENT DOCUMENTS

| 2,780,121 | 2/1957 | White | 72/458 |
| 4,052,881 | 10/1977 | Mount | 72/459 |
| 4,269,056 | 5/1981 | Kozinski | 72/459 |
| 5,201,210 | 4/1993 | Stein, III | 72/479 |

FOREIGN PATENT DOCUMENTS

| 1000663 | 1/1957 | Germany | 76/458 |
| 107310 | 5/1937 | United Kingdom | 72/459 |
| 980564 | 1/1965 | United Kingdom | 72/459 |

*Primary Examiner*—David Jones
*Attorney, Agent, or Firm*—Flehr Hohbach Test Albritton & Herbert

[57] ABSTRACT

A bending tool for use with a human hand for bending the distal extremity of a guide tube of a medical device having a needle assembly slidably mounted in the guide tube. The distal extremity of the guide tube has a tip. The bending tool is comprised of a shaft sized so that it is adapted to be grasped by the human hand to serve as a handle. The shaft has proximal and distal extremities and a longitudinal axis. A bending construction is mounted on the distal extremity of the shaft and provides a curved bending surface having width and a length and having a proximal and a distal extremity and extending at an angle with respect to the longitudinal axis. The bending construction also has an abutment surface at the distal extremity of the curved surface and extending generally perpendicular to the curved surface. The abutment surface has a hole therein extending in a direction generally perpendicular to the abutment surface and is sized so that it is adapted to receive the tip of the guide tube with the guide tube engaging the curved surface to permit bending of the guide tube by a swinging movement of the shaft in a direction at right angles to the abutment surface.

9 Claims, 2 Drawing Sheets

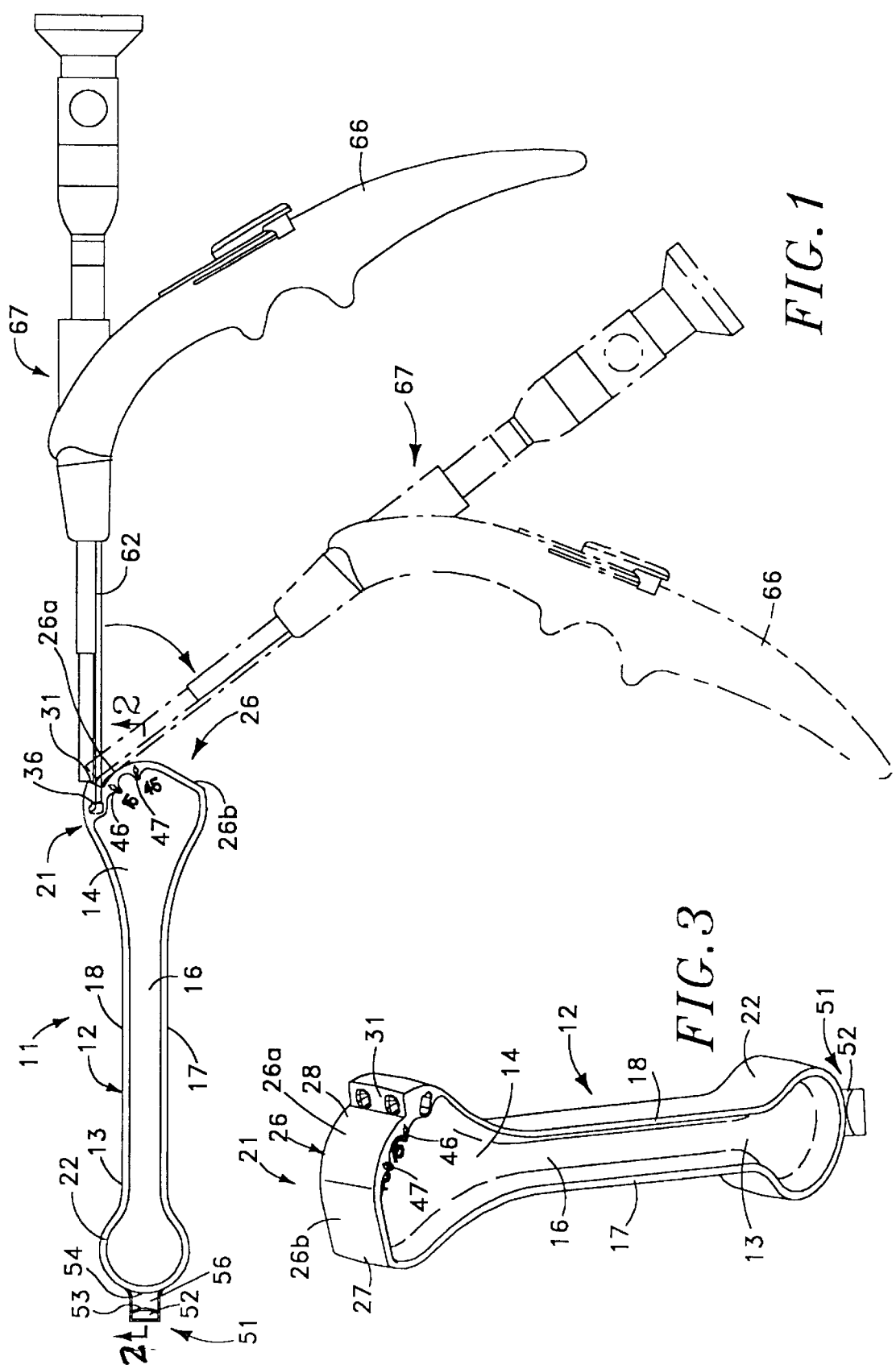

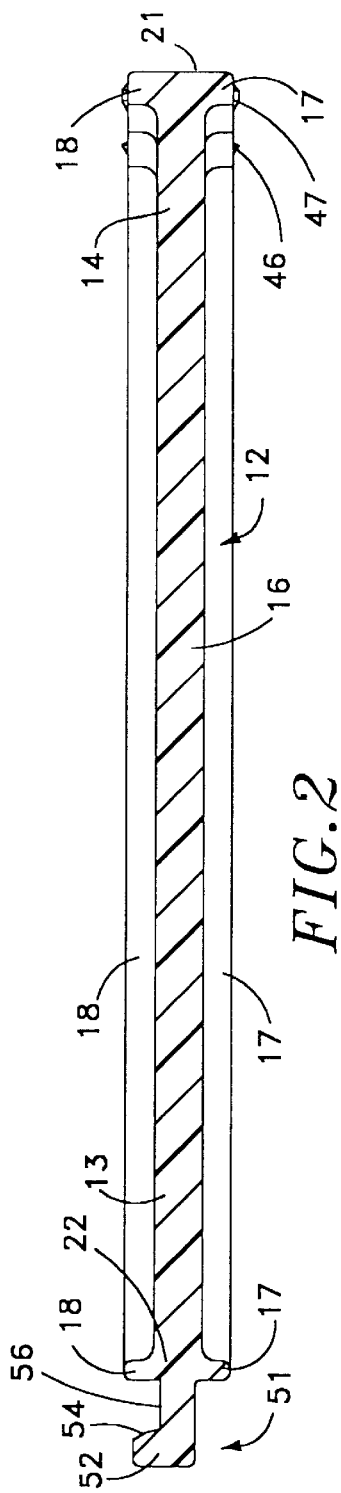
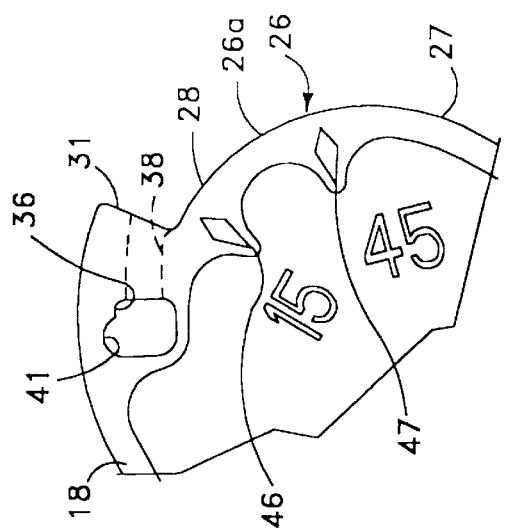
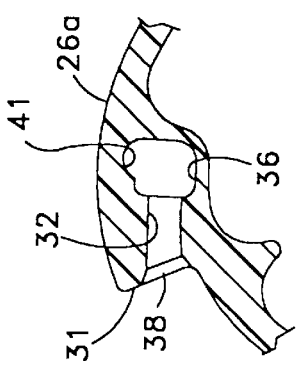
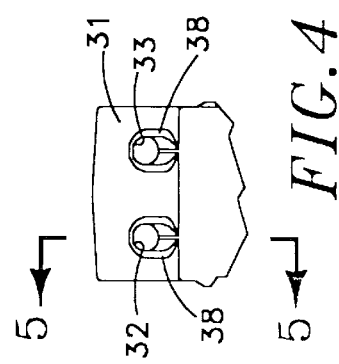

BENDING TOOL

This invention relates to a bending tool and more particularly to a bending tool for bending the distal extremity of a guide tube of a medical device having a needle slidably mounted in the guide tube.

Medical devices have heretofore been provided which have guide tubes therein through which needle assemblies are slidably mounted. Certain of such medical device have been provided with flexible distal extremities on the guide tubes and have been provided with means for bending the distal extremity so as to guide the needle assemblies slidably mounted therein in a predetermined direction. In certain applications, such medical devices have been found to be unduly expensive and complicated. There is therefore a need for less complicated medical devices and in which capabilities are provided for bending the distal extremities of the guide tubes so that the needle assemblies slidably mounted therein can be directed in predetermined directions at the time of use.

Another object of the invention is to provide a bending tool of a character which can be readily used by the hand to manually place a bend in the distal extremity of the guide tube at the time of use.

Another object of the invention is to provide a bending tool of the above character in which it is possible to bend the guide tube without kinking and crushing of the guide tube.

Another object of the invention is to provide a bending tool of the above character which can be utilized to bend the distal extremity of the guide tube with a uniform radius.

Another object of the invention is to provide a bending tool of the above character which does not place a bend which has less than a minimum bend radius.

Another object of the invention is to provide a bending tool of the above character which is provided with a bending surface which has small bumps therein to overcome crushing and kinking tendencies.

Another object of the invention is the provide a bending tool of the above character in which the tip of the guide tube is retained within the bending tool during the bending of the distal extremity to ensure that bending occurs from the tip proximally.

Another object of the invention is to provide a bending tool of the above character and which is provided with indicia so that the angle through which the bend will extend is readily determinable.

Another object of the invention is to provide a bending tool of the above character in which a predetermined bend can be provided in the distal extremity of the guide tube which compensates for spring back.

Another object of the invention is to provide a bending tool of the above character which is relatively simple and inexpensive to manufacture.

Additional objects and features of the invention will appear from the following description in which the preferred embodiment is set forth in detail in conjunction with the accompanying drawings.

FIG. 1 is a side elevational view of a bending tool incorporating the present invention.

FIG. 2 is a cross-sectional view taken along the line 2—2 of FIG. 1.

FIG. 3 is an enlarged isometric view of the bending tool shown in FIG. 1.

FIG. 4 is a partial elevational view of one end of the bending tool shown in FIG. 1.

FIG. 5 is a cross-sectional view taken along the line 5—5 of FIG. 4.

FIG. 6 is an enlarged side elevational detail view of the bending means forming a part of the bending tool.

In general, the bending tool of the present invention is for use with a human hand for bending the distal extremity of a guide tube of a medical device having a needle slidably mounted in the guide tube. The distal extremity of the guide tube has a tip. The bending tool comprises a shaft sized so as to be adapted to be grasped by the human hand to provide a handle. The shaft has proximal and distal extremities and a longitudinal axis. Bending means is mounted on the distal extremity of the shaft and provides a curved bending surface having a width and a length and having proximal and distal extremities with respect to the length and extending at an angle with respect to the longitudinal axis. Bending means is mounted on the distal extremity of the shaft and provides a curved bending surface having a width and length and having proximal and distal extremities and extending at an angle with respect to the longitudinal axis. The bending means also provides an abutment surface at the distal extremity of the curved surface and extending generally perpendicular to the curved surface. The abutment surface has a hole therein extending generally perpendicular to the abutment surface and is sized to receive the tip of the guide tube with the guide tube engaging the curved surface to permit bending of the guide tube as the shaft is swung in a direction at right angles to the abutment surface.

More in particular as shown in FIGS. 1 through 6 of the drawings, the bending tool 11 of the present invention is formed of a single piece of plastic as for example of polyphenylsulfone. The bending tool, however, can be made of a metal such as aluminum or other metal such as stainless steel. However, plastic has been chosen because of its light weight. Also, because it can be readily sterilized in the field.

The bending tool 11 is comprised of a shaft 12 having proximal and distal extremities 13 and 14. As can be seen particularly in FIG. 2, the shaft 12 has a cross-section resembling an I-beam which is provided with a vertically extending web 16 and spaced apart parallel flanges 17 and 18 disposed on opposite sides of the web 16 at right angles to the plane of the web 16 with the web 16 being secured to the flanges 17 and 18 at the mid-points of the flanges 17 and 18 by being formed integral therewith.

Bending means 21 is provided on the distal extremity 14 of the shaft 12 and a rounded enlargement 22 is provided on the proximal extremity 13. The I-beam type construction utilized for the shaft 12 also is utilized in the bending means 21 and also in the rounded enlargement 22 as shown in the drawings.

Let it be assumed that the bending tool 11 is to be utilized for bending the distal extremities of one or more guide tubes of a medical device having needle assemblies slidably mounted in the guide tubes. The distal extremities of the guide tube have tips which lie in a parallel plane. The guide tubes have a suitable size as for example ranging from 0.010" to 0.032". To accomplish bending of such guide tubes, the bending means 21 consists of a curved bending surface 26 which is shown in FIG. 3 having a width and a length and has proximal and distal extremities 27 and 28. The curved bending surface 26 is comprised of a curved surface 26a subtending at an angle of approximately 90° and a flat surface 26b adjoining the curved surface 26a and subtending a suitable angle as for example 45°. The radius of the curved surface 26a is selected so that it has a maximum bend radius and so that a bend is not inserted in the guide tube which is less than a predetermined minimum bend radius. It has been found that this is important when the guide tube is formed of a nickel-titanium alloy which upon being bent over to a sharp angle will create stress problems. Thus the curvature of the curved surface 26a controls the degree of bending of the guide tube as hereinafter described. By providing a predetermined radius for the curved surface 26a it is possible to bend the tube within predetermined limits while at the same time preventing collapsing or kinking of the guide tube.

The bending means 21 also includes an abutment surface 31 which extends outwardly and radially, generally in a perpendicular direction to the curved surface 26a. The abutment surface 31 is provided with first and second holes 32 and 33 which open through the abutment surface 31 and extend inwardly and open into a sidewise extending viewing port 36 formed in the bending means 21 carried by the distal extremity of the shaft 12. The holes 32 and 33 lie in a plane and are slightly ovoid in shape as shown in FIG. 4. Each of the holes 32 and 33 is provided with a chamfered inlet surface 38 as shown in FIGS. 4 and 5. As shown particularly in FIG. 5, the holes 32 become smaller in diameter as they extend into the viewing port 36. The viewing port 36 is generally rectangular in shape as shown particularly in FIGS. 5 and 6. An arcuate recess 41 is provided which extends along the axis of the viewing port 36 at the top portion of the viewing port to provide a free space into which the tips of the guide tubes can move during the time that they are being bent to prevent crushing of the tips of the guide tubes.

The bending means 21 is also provided with markers or indicia for indicating the degree of bending which is being placed in the guide tubes being bent by the bending tool and consists of first and second markers 46 and 47 provided on opposite sides of the bending means 21 with the markers being triangularly shaped and pointing respectively to 15° and 45° bends. The guide tubes are tangential on the surface 26 at these points indicated by the markers 46 and 47. If desired, the guide tubes can be bent through an additional angle up to approximately 90° including springback. The angles of 15° and 45° have been selected to provide such bends with approximately 6–7% springback of the guide tubes after they are released from the bending tool.

Reverse bending means 51 is provided on the proximal extremity 13 of the shaft 12. The reverse bending means 51 takes the form of an L-shaped member 52 formed integral with the rounded enlargement 22 which typically can have a suitable radius as for example ½" which is particularly desirable for use in straightening guide tubes of the type hereinbefore described. This L-shaped member 52 is provided with a curved surface 53 that has a convex shape facing towards the curved surface 54 of the rounded enlargement 22. The curved surface 53 has its curvature extending about an axis which is perpendicular to the longitudinal axis 19 of the shaft 12. The distance between the curved surfaces 53 and 54 provides a slot 56 having a suitable width as for example 0.05".

Operation and use of the bending tool 11 may now be briefly described as follows. Let it be assumed that it is desired to bend the distal extremity 61 of first and second guide tubes 62 disposed in a parallel plane carried by a handle 66 of a tissue ablation apparatus 67 of the type disclosed in co-pending application Ser. No. 08/941,401 filed Sep. 30, 1997 (A-64861). As disclosed therein, the guide tubes 62 carry needle assemblies (not shown) which are slidably mounted therein and adapted to be deployed through the guide tubes 62. Let it be assumed that the tissue ablation apparatus 67 has been provided with guide tubes 62 which are straight and that the physician utilizing the same wishes to access soft tissue in which the needle assemblies carried thereby are desired to be directed at an angle with respect to the longitudinal axis of the handle 66 of the tissue ablation apparatus and it is desired to place a bend in the guide tubes 62 as for example a 15° bend or alternatively a 45° bend. This can be readily accomplished by the physician holding the tissue ablation apparatus 67 in one hand and then grasping the shaft 12 of the bending tool 11 in the other hand and then with the needle assemblies (not shown) retracted placing the guide tubes 62 in the holes 32 and 33 provided in the abutment surface 31 until their distal extremities can be viewed through the viewing port 36. While holding the tissue ablation apparatus 67 in a stationary position in one hand, the bending tool 11 can be curved or swung in a direction toward the tissue ablation apparatus 67 until the desired amount of bend has been placed in the guide tube 62. The amount of bending being placed in the guide tube 62 can be readily observed by watching the markers 46 and 47. After the desired amount of bend has been placed in the guide tube 62, the forces being applied to the guide tubes 62 can be released and the bending tool 11 removed from the distal extremities of the guide tube 62. The tissue ablation apparatus is then ready for use.

When the bending tool 11 of the present invention is being utilized for placing bends in the guide tubes 62, this is accomplished by bending the tubes with a uniform radius as determined by the curved surface 26a. The curved surface 26a also dictates the bend which can be placed in the guide tubes 62, thereby ensuring that undue stresses are not placed in the guide tubes which is particularly important if they are formed of a nickel-titanium alloy as pointed out above. This bending occurs without any kinking or crushing of the guide tubes 62. It also prevents crushing of the very tips of the distal extremities of the guide tubes 62 by providing free space within the viewing port 36 as provided by the arcuate recess 41 permitting the tips of the guide tubes 62 to roll and rock upwardly as the bending is occurring, thereby preventing damage to the tips of the guide tubes 62.

As hereinbefore explained, the markers 46 and 47 have been positioned so as to accommodate approximately a 6–7% springback of the guide tubes 62 when they are released from the bending tool 11.

In the event it is desired to place a still greater bend in the distal extremities of the guide tubes 62, this can be readily accomplished by reinserting the guide tubes 62 into the holes 32 and 33 and swinging the tool with respect to the tissue ablation apparatus to cause greater bends to be placed in the guide tubes 62 after which the bending tool 11 can be released.

If it is desired to straighten a guide tube or tubes 62 after they have been bent in the manner hereinbefore described, this can be accomplished by utilizing the reverse bending means 51 provided on the proximal extremity 13 and mounted on the rounded enlargement 22. The guide tubes 62 are positioned within the slot or gap 56 and the guide tubes 62 of the tissue ablation device can be progressively walked down the needle while at the same time applying straightening forces by sequentially rocking the proximal extremity 13 of the tool 11 back and forth causing the guide tubes 62 to successively engage the curved surface 54 and then the curved surface 53. This procedure which can be called reverse bending is continued until the guide tubes 62 have been straightened in the amount desired. This reverse bending or straightening occurs without kinking or crushing of the guide tubes 62.

From the foregoing it can be seen that there has been provided a bending tool which has unique capabilities for the bending of the distal extremities of medical devices as for example tissue ablation devices permitting the physician or doctor utilizing the tissue ablation apparatus to place the desired bend in the guide tubes. It also permits the physician to straighten guide tubes after they have been bent if this is desired by utilizing the same tool. The tool is of a type which is economical to manufacture and which can be readily sterilized so that it can be used repeatedly.

What is claimed:

1. A bending tool for use with a human hand for bending the distal extremity of a guide tube of a medical device having a needle assembly slidably mounted in the guide tube, the distal extremity of the guide tube having a tip, the bending tool comprising a shaft sized so that it is adapted to be grasped by the human hand to provide a handle, the shaft having proximal and distal extremities and a longitudinal axis, bending means mounted on the distal extremity of the shaft and providing a curved bending surface having width and a length and having a proximal and a distal extremity and extending at an angle with respect to the longitudinal axis, said bending means also having an abutment surface at the distal extremity of the curved surface and extending generally perpendicular to the curved surface, said abutment surface having a hole therein extending in a direction generally perpendicular to the abutment surface and sized so it is adapted to receive the tip of the guide tube with the guide tube engaging the curved surface to permit bending of the guide tube by a swinging movement of the shaft in a direction at right angles to the abutment surface.

2. A bending tool as in claim 1 wherein said bending means includes spaced-apart markers formed on the bending means indicating the degree of bending of the guide tube as the shaft is swung.

3. A bending tool as in claim 1 wherein said bending means includes a port extending at right angles to the hole to provide a space for the tip of the distal extremity of the guide tube to move when bending forces are being applied to the guide tube to prevent damage to the tip of the distal extremity of the guide tube.

4. A bending tool as in claim 3 wherein said port is substantially rectangular in cross-section and has a transversely extending arcuate slot formed therein in the upper side thereof to provide free space in which the tip of the guide tube can move.

5. A bending tool as in claim 1 further comprising a rounded enlargement secured to the proximal extremity of the shaft of the tool.

6. A bending tool as in claim 5 together with reverse bending means mounted on the rounded enlargement, said reverse bending means including an L-shaped member secured to the rounded enlargement and having a curved surface facing the rounded enlargement and forming a slot therewith through which a guide tube can be inserted to permit straightening of the guide tube.

7. A bending tool as in claim 1 wherein said bending tool is formed of plastic.

8. A bending tool as in claim 1 wherein said shaft has a cross-section corresponding to an I-beam.

9. A bending tool as in claim 1 wherein said curved surface has a curved portion and a flat portion adjoining the curved portion.

* * * * *